US006319874B1

(12) United States Patent
Winter et al.

(10) Patent No.: US 6,319,874 B1
(45) Date of Patent: Nov. 20, 2001

(54) METHOD FOR PRODUCING METALLOCENES

(75) Inventors: Andreas Winter, Glashütten; Carsten Bingel, Kriftel; Volker Fraaije, Frankfurt; Frank Kueber, Oberursel, all of (DE)

(73) Assignee: Basell Polyolefine GmbH, Ludwigshafen (DE)

( * ) Notice: Subject to any disclaimer, the term of this patent is extended or adjusted under 35 U.S.C. 154(b) by 0 days.

(21) Appl. No.: 09/462,584

(22) PCT Filed: Jul. 23, 1998

(86) PCT No.: PCT/EP98/04630

§ 371 Date: Jan. 11, 2000

§ 102(e) Date: Jan. 11, 2000

(87) PCT Pub. No.: WO99/05153

PCT Pub. Date: Feb. 4, 1999

(30) Foreign Application Priority Data

Jul. 28, 1997 (DE) .............................................. 197 32 366

(51) Int. Cl.[7] ............................... B01J 31/38; C08F 4/16; C08F 4/76

(52) U.S. Cl. .......................... 502/152; 502/104; 502/117; 526/160; 526/943; 526/75; 556/53

(58) Field of Search .................................... 526/160, 161, 526/170, 171, 172, 943, 127, 75; 502/102, 117, 152, 155; 556/53

(56) References Cited

U.S. PATENT DOCUMENTS 5,239,022 8/1993 Winter et al. ........................ 526/127
5,276,208 1/1994 Winter et al. .......................... 556/53
5,304,614 4/1994 Winter et al. ........................ 526/127
5,910,464 * 6/1999 Resconi et al. ...................... 502/111

FOREIGN PATENT DOCUMENTS 185 918 7/1986 (EP) .
344 887 12/1989 (EP) .
485 820 5/1992 (EP) .
485 821 5/1992 (EP) .
537 686 4/1993 (EP) .

OTHER PUBLICATIONS

J. Org. Chem 497 (1995) 181–193, Kaminsky et al.

Angew Chem. 1992, 104,, No. 10, 1373–1376–Spaleck et al.

Organometallics 1993, 12, 4391–4401, Ellis et al.

Chem. Ber. 1994, 127 2417–1429, Rieger et al.

Macromolecules 1994, 27, 4477–4485, Kelly et al.

Macromolecules, vol. 29, No. 7, 3/35/96, Rossi et al.

J. Molecular Catalysis A:Chem. 102 (1995) 59–65, Schupfer et al.

Organometallics 1991, 10, 1501–1505, Grossmann et al.

J. Organo. Chem, 342 (1988) 21–29, Collins et al.

J. Organ. Chem. 520 (1996) 163–170, Halterman.

Chem Abstracts, Columbus, Ohio, vol. 124, 1366, 124:289746J 1996.

* cited by examiner

*Primary Examiner*—David W. Wu
*Assistant Examiner*—R. Harlan
(74) *Attorney, Agent, or Firm*—Keil & Weinkauf

(57) ABSTRACT

A process for preparing rac/meso-metallocenes, the rac/meso-metallocenes themselves and the use of the rac/meso-metallocenes for preparing isotactic polyolefins are described.

13 Claims, No Drawings

METHOD FOR PRODUCING METALLOCENES

The present invention relates to a process for preparing rac/meso-metallocenes, the rac/meso-metallocenes themselves and the use of the rac/meso-metallocenes as catalyst components for preparing isotactic polyolefins.

Racemic metallocenes (rac-metallocenes) containing partially hydrogenated or hydrogenated p ligands have been described as catalyst precursors for the polymerization of olefins, for example in J. Organomet. Chem. 497(1995)181, Angew. Chem. 104 (1992) 1373, Organometallics 12 (1993) 4391 or Chem. Ber. 127 (1994) 2417, J. Am. Chem. Soc. 118 (1996) 2105, Macromolecules 27 (1994) 4477 or Macromolecules 29 (1996) 2331, EPA 0 344 887, J. Mol. Catal. A. Chem. 102 (1995) 59, EPA 0 185 918, EPA 0 537 686, EP 0 485 820 or EP 0 485 821.

In the synthesis of metallocenes, great effort is made to isolate the racemic form of the metallocene, since only this form enables, for example, isotactic polypropylene to be prepared stereospecifically. The meso form of the metallocene is separated off. In the preparation of metallocenes containing partially hydrogenated or hydrogenated p ligands, the racemic form of the unhydrogenated metallocene is isolated first and then hydrogenated. Thus, for example, rac-dimethylsilanediylbis-(4,5,6,7-tetrahydroindenyl)zirconium dichloride can be prepared from rac-dimethylsilanediylbisindenylzirconium dichloride by hydrogenation of the octahydro derivative. Such and similar reactions are described, for example, in EPA 0 344 887, J. Organomet. Chem. 497 (1995) 181, Organometallics 10 (1991) 1501 or J. Organomet. Chem. 342 (1988) 21.

The known synthetic procedures for hydrogenating the aromatic ligand skeleton of rac-metallocenes all in principle follow the same route. The purified rac-metallocene is dissolved or suspended in dichloromethane and hydrogenated under a high hydrogen pressure in the presence of platinum black or platinum dioxide (cf. J. Organomet. Chem. 342 (1988) 21 or EPA 0 344 887).

Dichloromethane and other chlorinated solvents can only be used in relatively large amounts with observance of strict occupational hygiene measures and environmental regulations. Only low-activity hydrogenation catalysts such as platinum black or platinum dioxide can be used in chlorinated solvents so as to avoid dehalogenation reactions. The dehalogenation reactions lead to decomposition of the product and to corrosion problems.

It is an object of the present invention to provide an efficient, rapid, inexpensive and yield-optimized direct synthesis of metallocenes by means of which highly isotactic polyolefins can be prepared inexpensively.

We have found that this object is achieved by a process for the direct preparation of rac/meso-metallocenes containing tetrahydroindenyl ligands. The rac/meso-metallocenes prepared according to the present invention can, surprisingly, be used directly as catalyst component for olefin polymerization without an additional, costly and yield-reducing isolation of the rac-form being necessary.

The present invention accordingly provides a process for preparing an rac/meso-metallocene of the formula I having an rac/meso ratio of from >20:1 to <200:1, Formula I

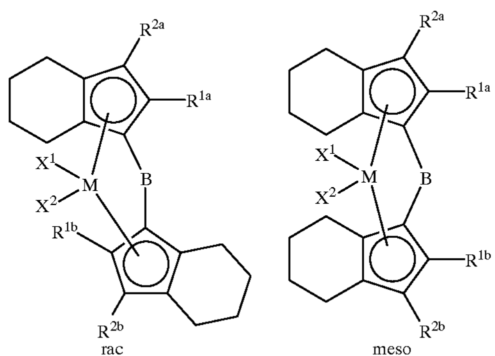

where

M is a metal of group IIIb, Ivb, Vb or VIb of the Periodic Table of the Elements and is preferably a metal of group Ivb, i.e. Ti, Zr or Hf, particularly preferably Zr or Hf, the radicals $X^1$ and $X^2$ (in the following also collectively referred to as X) are identical or different, preferably identical, are each a hydrogen atom, a $C_1$–$C_{40}$-group such as $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen such as nitrile, with preference being given to linear or branched $C_1$–$C_{10}$-alkyl and halogen atoms and very particular preference being given to chlorine and methyl, the radicals $R^{1a}$ and $R^{1b}$ (in the following also collectively referred to as $R^1$), and $R^{2a}$ and $R^{2b}$ (in the following also collectively referred to as $R^2$), are identical or different and are each a hydrogen atom, a $C_1$–$C_{40}$-group such as $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen such as nitrile, or a $NR^5_2$, $OSiR^5_3$ or $PR^5_2$ group with $R^5$ defined as for X, with preference being given to the radicals $R^2$ being identical and each being a hydrogen atom and the radicals $R^1$ being identical and each being hydrogen or linear or branched $C_1$–$C_{10}$-alkyl, B is a bridge between the indenyl ligands which may be, for example, from single- to four-membered, with preference being given to single- and two-membered bridges, comprising the steps:

a) reaction of a substituted cyclopentadiene of the formula A (A)

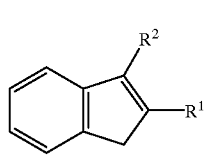

with a bridging reagent $BY_2$ to form a bridged biscyclopentadienyl ligand system, b) reaction of the bridged biscyclopentadienyl ligand system with a metal halide to form a metallocene of the formula Ia, c) hydrogenation of the metallocene of the formula Ia to form a metallocene of the formula Ib d) and, if desired, reaction of a metallocene of the formula Ib with an organometallic compound $R^3M^1$ to form a metallocene of the formula Ic, where all steps are carried out in the same solvent or solvent mixture.

The invention further provides chiral rac/meso-metallocenes of the formula I having an rac/meso ratio of from >20:1 to <200:1

Formula I

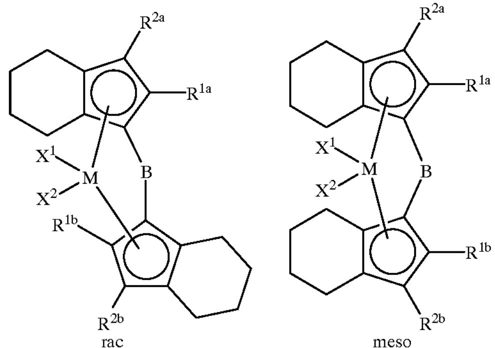

where

M is a metal of group IIIb, IVb, Vb or VIb of the Periodic Table of the Elements and is preferably a metal of group IVb, i.e. Ti, Zr or Hf, particularly preferably Zr or Hf, the radicals $X^1$ and $X^2$ (in the following also collectively referred to as X) are identical or different and are each a hydrogen atom, a $C_1$–$C_{40}$-group such as $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen such as nitrile, with preference being given to linear or branched $C_1$–$C_{10}$-alkyl and halogen atoms and very particular preference being given to chlorine and methyl, the radicals $R^{1a}$ and $R^{1b}$ (in the following also collectively referred to as $R^1$), and $R^{2a}$ and $R^{2b}$ (in the following also collectively referred to as $R^2$) are identical or different and are each a hydrogen atom, a $C_1$–$C_{40}$-group such as $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen such as nitrile, or an $NR^5_2$, $OSiR^5_3$ or $PR^5_2$ group where $R^5$ is defined as for X, with preference being given to the radicals $R^2$ being identical and each being a hydrogen atom and the radicals $R^1$ being identical and being hydrogen or linear or branched $C_1$–$C_{10}$-alkyl, B is a bridge between the tetrahydroindenyl ligands which can, for example, be from single- to four-membered, with preference being given to single- and two-membered bridges.

The invention also provides a catalyst comprising a) at least one chiral rac/meso-metallocene of the formula I and b) at least one cocatalyst and also provides for the use of the catalyst for the polymerization of olefins or in a process for the polymerization of olefins.

In the process of the present invention, the ligand system is prepared first and, without isolating the bridged bisindenyl ligand system, the rac/meso-metallocene of the formula Ia is then prepared and subsequently hydrogenated to form the bistetrahydroindenyl metallocene of the formula Ib. The rac/meso-metallocene of the formula Ib can be reacted further to give the rac/meso-metallocene of the formula Ic.

Scheme 1

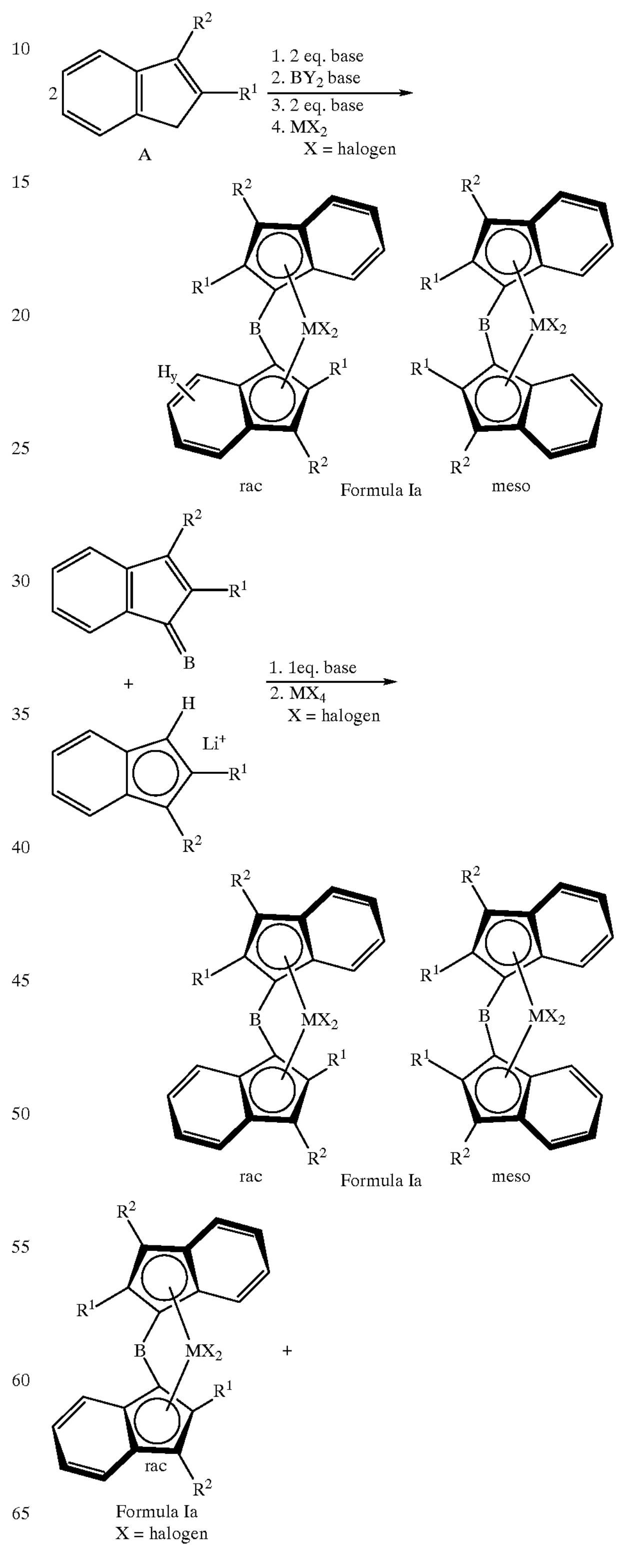

-continued

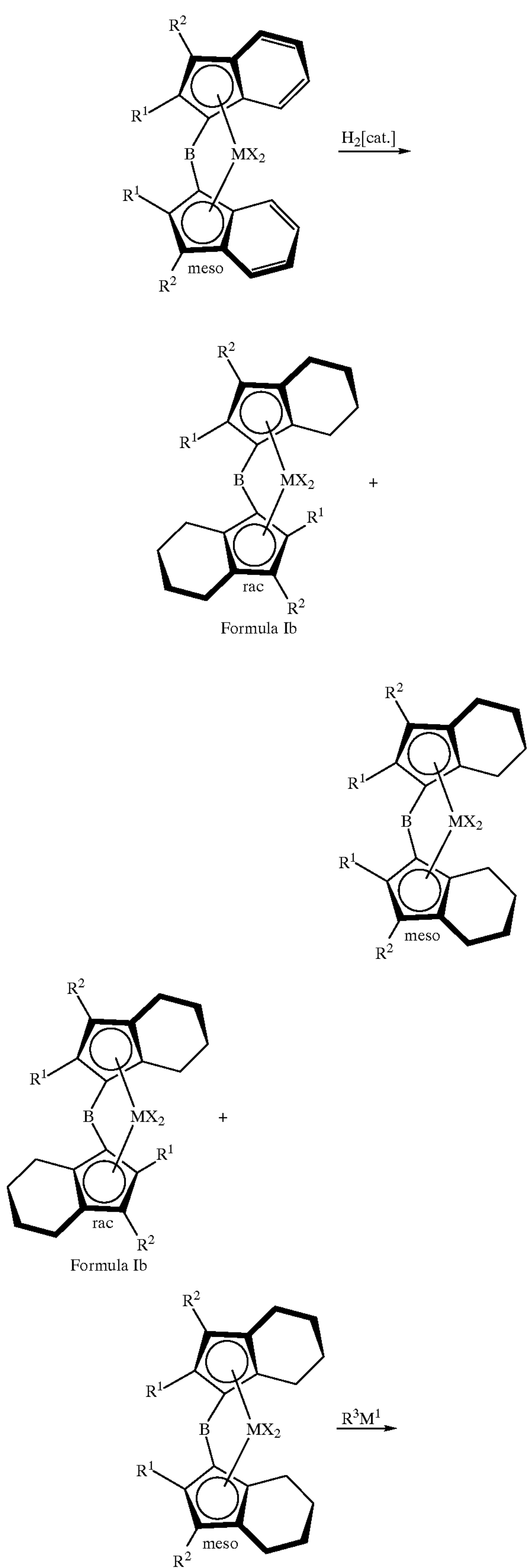

-continued

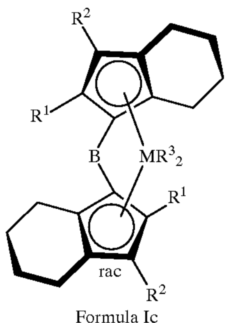

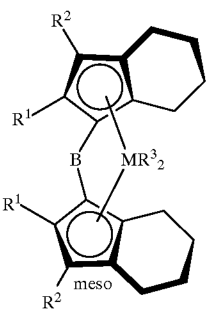

As illustrated in Scheme 1, the process starts with the preparation of a bridged bisindenyl system from an indene of the formula A by deprotonation using a strong base such as butyllithium or potassium hydride in a suitable solvent or solvent mixture and addition of a bridging reagent $BY_2$. Here, B is as defined in formula I and Y is a leaving group such as halogen. The bridged bisindenyl system is further deprotonated using a strong base such as butyllithium or potassium hydride and then reacted with a metal halide of group IIIb, IVb, Vb or VIb of the Periodic Table of the Elements, preferably with a halide of titanium, zirconium or hafnium, particularly preferably zirconium tetrachloride or hafnium tetrachloride, to give the rac/meso-metallocene of the formula Ia. The metal halides can also be used in the form of ligand-containing complexes such as $HfCl_4(THF)_2$, $ZrCl_4(THF)_2$, $TiCl_4(THF)_2$, $TiCl_3(THF)_3$, $VCl_3(THF)_3$ or $ScCl_3(THF)_3$.

The bridge B is introduced by reacting the metallated indenyl with a compound of the formula $BY_2$. The compound $BY_2$ is preferably a compound such as $(CH_3)_2SiCl_2$, $(CH_3)(C_6H_5)SiCl_2$, $CH_2Br_2$, $(CH_3)_2CBr_2$ or 1,2-dibromoethane.

To introduce a $C_1$ bridge, an alternative is to react the corresponding benzofulvene with one equivalent of the metallated indenyl. In these cases, B is preferably $CH_2$, $C(CH_3)_2$, $C(CH_3)(C_6H_5)$ or $C(C_6H_5)_2$.

Suitable solvents for the single-vessel synthesis are aliphatic or aromatic solvents such as hexane or toluene, preferably aromatic solvents, or ether solvents such as tetrahydrofuran (THF), diethyl ether or dimethoxyethane (DME) or else solvent mixtures of the abovementioned solvent classes, for example toluene/THF, toluene/DME, toluene/hexane/THF or hexane/diethyl ether.

After the synthesis of the complex, the above-described rac/meso-metallocene of the formula Ia can be isolated or the rac/meso-metallocene-containing reaction mixture is subjected directly to hydrogenation.

To isolate the rac/meso-metallocene of the formula Ia, the precipitated rac/meso-metallocene together with the inorganic salt formed can be filtered off or else the rac/meso-metallocene is kept in solution in a sufficient amount of the solvents used in the metallocene synthesis, preferably an aromatic solvent such as toluene, and separated from the inorganic salt by filtration.

The rac/meso-metallocene isolated as a filter cake may, if desired, be washed and dried. The rac/meso-metallocene can subsequently be separated from salt-like constituents. The rac/meso-metallocene present in solution may, if desired, be freed of solvent and isolated as a solid. The rac/meso-metallocene obtained can be obtained in pure form or as a mixture with further constituents such as inorganic salts.

Examples of further constituents are inorganic salts such as LiCl, LiBr, NaCl, NaBr, KCl, KBr, $MgCl_2$, $MgBr_2$, MgBrCl, $CaCl_2$, $AlCl_3$ and also filter aids such as $Na_2SO_4$, quartz flour and Celite. Further constituents can also be organic and organometallic secondary components. Organic secondary components are solvent residues, organic impurities from the starting materials, unreacted starting materials and incompletely reacted intermediates of the metallocene synthesis. Organometallic secondary components can be isomeric metallocenes, oligomeric metallocenes and compounds which are introduced via impurities in the starting compounds.

After its preparation, the rac/meso-metallocene of the formula Ia can be converted directly into the corresponding tetrahydroindenyl derivative of the formula Ib. The hydrogenation of the rac/meso-metallocene of the formula Ia is carried out as described above using hydrogen in an aromatic or oxygen-containing aprotic solvent in the presence of at least one hydrogenation catalyst.

Aromatic solvents are solvents which contain at least one aromatic six-membered ring per molecule. Examples of aromatic solvents are benzene, toluene, xylene (as isomer mixture), o-xylene, m-xylene, p-xylene, mesitylene, tetralin, anisole, cumene, 1,2-diethylbenzene, 1,3-diethylbenzene, 1,4-diethylbenzene, 1-ethyl-2-methylbenzene, 1-ethyl-3-methylbenzene and 1-ethyl-4-methylbenzene. Preference is given to anisole, toluene, benzene, xylenes (as a mixture or pure material) and tetralin.

Oxygen-containing aprotic solvents include aromatic and aliphatic ethers such as anisole, ethyl phenyl ether, isopropyl phenyl ether, diethyl ether, di-n-butyl ether, tert-butyl methyl ether, tetrahydrofuran and dioxane. It is also possible to use esters of aliphatic or aromatic carboxylic acids as solvents, for example ethyl acetate and propyl butyrate.

The process described is carried out in a temperature range from 0° C. to 150° C.; in particular, the hydrogenation is carried out at from 15° C. to 100° C.

Suitable hydrogenation catalysts are compounds or elements which do not hydrogenate or only partially hydrogenate the solvent under the hydrogenation conditions employed. Examples of such hydrogenation catalysts are palladium on activated carbon, palladium on barium sulfate, palladium on aluminum oxide, palladium black, palladium sponge, platinum oxide, platinum black and platinum sponge. Preference is given to palladium catalysts, in particular palladium on activated carbon.

The pure hydrogenated rac/meso-metallocene of the formula Ib or this metallocene mixed with further constituents prepared as described above can be further reacted with an organometallic compound $R^3M^1$ to give the rac/meso-metallocene of the formula Ic or can be used directly as catalyst component in the polymerization.

In the compound $R^3M^1$, $M^1$ is an element of main groups I to III, preferably lithium, magnesium or aluminum, and $R^3$ is defined as for X in formula I, apart from halogen. If the rac/meso-metallocene of the formula Ia is to be able to be isolated, particular preference is given to organometallic compounds in which the radical $R^3$ bears no aliphatic β-hydrogen atom. Examples of such compounds are organolithium compounds such as $CH_3Li$, benzyllithium and $C_6H_5Li$, and also Grignard compounds such as $CH_3MgCl$, $CH_3MgBr$, $CH_3MgI$, benzylMgBr, $C_6H_5MgCl$ and organoaluminum compounds such as trimethylaluminum or methylaluminoxane.

The reaction is carried out in a solvent or solvent mixture which is inert toward $R^3M^1$. Suitable solvents are aliphatic or aromatic solvents such as hexane or toluene, ether solvents such as tetrahydrofuran (THF), diethyl ether or dimethoxyethane (DME) as well as solvent mixtures from among the abovementioned solvent classes, for example toluene/THF, toluene/hexane/THF or hexane/diethyl ether.

The replacement of the halogen atoms on the transition metal is carried out at from −100° C. to the boiling point of the solvent or solvent mixture used, preferably at from −78° C. to the boiling point of the solvent or solvent mixture used.

After the reaction is complete, the rac/meso-metallocene of the formula Ib can be separated off, for example by extraction of the metal halide formed, and isolated by crystallization; during this procedure, the rac/meso ratio can be changed from that in the starting material.

Rac/meso-metallocenes which are silyl-bridged bistetrahydroindenyl complexes of hafnium or zirconium are preferably prepared as follows: 1 equivalent of indene is deprotonated at from room temperature to 50° C. in a toluene/THF mixture in a ratio of from 100:1 to 1:5, preferably from 20:1 to 2:1, using a solution of n-butyllithium (preferably 1 equivalent) and subsequently admixed at from −30° C. to room temperature with half an equivalent of an alkyl- and/or aryl-substituted dichlorosilane, e.g. dimethyldichlorosilane, and stirred for a further period of from 1 to 5 hours at a temperature of from room temperature to 60° C. The intermediate is subsequently deprotonated at from room temperature to 50° C. using a further equivalent of butyllithium, stirred for a further period of from 1 to 5 hours at from room temperature to 50° C. and reacted at from −30° C. to 50° C., preferably from −10° C. to room temperature, with from 0.4 to 1 equivalent, preferably from 0.45 to 0.75 equivalent, of the tetrachloride of zirconium or hafnium and subsequently stirred for a further period of from 1 to 5 hours. In the case of dimethylsilylbisindenylzirconium dichloride, the suspension of the complex from the single-vessel synthesis is filtered and the solid is washed with toluene or THF, preferably THF. The filter cake, which comprises rac/meso-dimethylsilylbisindenylzirconium dichloride, is suspended in toluene, admixed with palladium on carbon and hydrogenated at from 20° C. to 120° C., preferably from 50° C. to 90° C., and a hydrogen pressure of from 5 to 100 bar, preferably from 10 to 50 bar. Rac/meso-dimethylsilylbis(tetrahydroindenyl)zirconium dichloride is separated from inorganic by-products by toluene extraction and isolated as solid after removing a major part of the solvent.

The novel process surprisingly has many advantages. The ligand synthesis and the synthesis of the rac/meso-metallocene of the formula Ia itself are carried out in the same reaction vessel and, furthermore, the synthesis of the complex can be carried out using the same non-chlorinated solvents which can be used in the subsequent hydrogenation to form a rac/meso-metallocene of the formula Ib and can be used in the replacement of the halogen atoms X on the transition metal M to form a rac/meso-metallocene of the formula Ic.

The use of non-chlorinated solvents enables more effective hydrogenation catalysts to be used and the reactions can be carried out at relatively low hydrogen pressures. This is of particular interest for industrial applications. The chlorinated solvents which are of concern from safety and environmental points of view are avoided. The use of aromatic hydrocarbons or slightly polar aprotic solvents such as ethers makes the subsequent work-up of the metallocenes easier. In the case of the preferred solvents such as anisole, toluene, benzene, xylene, tert-butyl methyl ether and tetrahydrofuran, it is possible to completely dissolve the product at elevated temperature, separate off the hydrogenation catalyst and inorganic salt-like by-products and crystallize the product or use the solution directly as catalyst component in the polymerization. The good solubility of the hydrogenated products in aromatic solvents at elevated temperature makes it possible to hydrogenate very concentrated metallocene suspensions, which is an advantage in terms of a good space-time yield. In addition, the amounts of hydrogenation catalyst required are significantly cheaper than in known processes.

The present invention is illustrated below by way of example.

The rac/meso-metallocenes prepared in the process of the present invention are compounds of the formula I in an rac/meso ratio of from >20:1 to <200:1, preferably from >30:1 to <100:1, particularly preferably from >35:1 to <60:1, very particularly preferably from >40:1 to <50:1.

Formula I

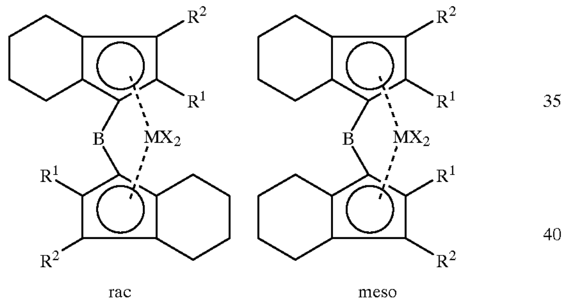

where

M is a metal of group IIIb, IVb, Vb or VIb of the Periodic Table of the Elements and is preferably a metal of group IVb, i.e. Ti, Zr or Hf, particularly preferably Zr or Hf, the radicals X are identical or different, preferably identical, are each a hydrogen atom, a $C_1$–$C_{40}$-group such as $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen such as nitrile, with preference being given to linear or branched $C_1$–$C_{10}$-alkyl and halogen atoms and very particular preference being given to chlorine and methyl, the radicals $R^1$ and $R^2$ are identical or different, with even radicals having the same index being able to be different, and are each a hydrogen atom, a $C_1$–$C_{40}$-group such as $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen such as nitrile, or a $NR^5_2$, $SR^5$, $OSiR^5_3$, $SiR^5_3$ or $PR^5_2$ group with $R^5$ defined as for X, with preference being given to the radicals $R^2$ being identical and each being a hydrogen atom and the radicals $R^1$ being identical and each being hydrogen or linear or branched $C_1$–$C_{10}$-alkyl, B is a bridge between the indenyl ligands which may be, for example, from single- to four-membered, with preference being given to single- and two-membered bridges.

Examples of such bridges are

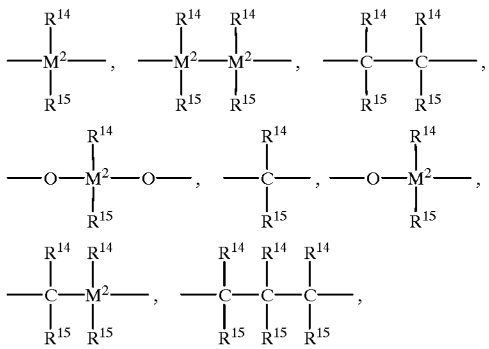

$=BR^{14}$, $=AlR^{14}$, —Ge—, —O—, —S—, =SO, $=SO_2$, $=NR^{14}$, =CO, $=PR^{14}$ or $=P(O)R^{14}$, where $R^{14}$ and $R^{15}$ are identical or different and are each a hydrogen atom, a halogen atom or a $C_1$–$C_{40}$-hydrocarbon-containing group such as $C_1$–$C_{10}$-, in particular $C_1$–$C_4$-alkyl group, a $C_1$–$C_{10}$-fluoroalkyl group, in particular a $CF_3$ group, a $C_6$–$C_{10}$-, in particular $C_6$–$C_8$-aryl group, a $C_6$–$C_{10}$-fluoroaryl group, in particular a pentafluorophenyl group, a $C_1$–$C_{10}$-, in particular $C_1$–$C_4$-alkoxy group, in particular a methoxy group, a $C_2$–$C_{10}$-, in particular $C_2$–$C_4$-alkenyl group, a $C_7$–$C_{40}$-, in particular $C_7$–$C_{10}$-arylalkyl group, a $C_8$–$C_{40}$-, in particular $C_8$–$C_{12}$-arylalkenyl group, a $C_7$–$C_{40}$-, in particular $C_7$–$C_{12}$-alkylaryl group or $R^{14}$ and $R^{15}$ together with the atoms connecting them form a ring and $M^2$ is silicon, germanium or tin.

The bridge B is preferably

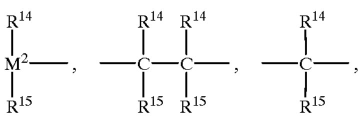

where $M^2$ is silicon or germanium and $R^{14}$ and $R^{15}$ are identical or different and are each a $C_1$–$C_4$-alkyl group or a $C_6$–$C_{10}$-aryl group.

$R^{14}$ and $R^{15}$ are identical or different and are preferably hydrogen, a $C_1$–$C_4$-alkyl group, in particular a methyl group, a $CF_3$ group, a $C_6$–$C_8$-aryl group, a pentafluorophenyl group, a $C_1$–$C_{10}$-, in particular $C_1$–$C_4$-alkoxy group, in particular a methoxy group, a $C_2$–$C_4$-alkenyl group, a $C_7$–$C_{10}$-arylalkyl group, a $C_8$–$C_{12}$-arylalkenyl group or a $C_7$–$C_{12}$-alkylaryl group.

B is particularly preferably a $R^{14}R^{15}C=$, $R^{14}R^{15}Si=$ or $—CR^{14}R^{15}—CR^{14}R^{15}—$ bridge, where $R^{14}$ and $R^{15}$ are identical or different and are each a hydrogen atom, a $C_1$–$C_4$-alkyl group or a $C_6$–$C_{10}$-aryl group.

The particularly preferred rac/meso-metallocenes of the formula I comprise combinations of the following molecular fragments:

B: $—CH_2—CH_2—$, $(H_3C)_2Si=$ or $(H_3C)_2C=$, preferably $(H_3C)_2Si=$ $MX_2$: —$ZrCl_2$, —$HfCl_2$, —$Zr(CH_3)_2$, —$Hf(CH_3)_2$ Ligand: tetrahydroindenyl Examples of rac/meso-metallocenes of the formula I are listed below:

rac/meso-dimethylsilanediylbis(4,5,6,7-tetrahydro-1-indenyl)-zirconium dichloride rac/meso-dimethylmethylenebis(4,5,6,7-tetrahydro-1-indenyl)-zirconium dichloride rac/meso-ethanediylbis(4,5,6,7-tetrahydro-1-indenyl) zirconium dichloride rac/meso-dimethylsilanediylbis(4,5,6,7-tetrahydro-1-indenyl)dimethylzirconium rac/meso-dimethylmethylenebis(4,5,6,7-tetrahydro-1-indenyl)dimethylzirconium rac/meso-ethanediylbis(4,5,6,7-tetrahydro-1-indenyl) dimethylzirconium rac/meso-dimethylsilanediylbis(4,5,6,7-tetrahydro-1-indenyl)hafnium dichloride rac/meso-dimethylmethylenebis(4,5,6,7-tetrahydro-1-indenyl)hafnium dichloride rac/meso-ethanediylbis(4,5,6,7-tetrahydro-1-indenyl) hafnium dichloride rac/meso-dimethylsilanediylbis(4,5,6,7-tetrahydro-1-indenyl)dimethylhafnium rac/meso-dimethylmethylenebis(4,5,6,7-tetrahydro-1-indenyl)dimethylhafnium rac/meso-ethanediylbis(4,5,6,7-tetrahydro-1-indenyl) dimethylhafnium rac/meso-dimethylsilanediylbis(2-alkyl-4,5,6,7-tetrahydro-1-indenyl)zirconium dichloride rac/meso-dimethylmethylenebis(2-alkyl-4,5,6,7-tetrahydro-1-indenyl)zirconium dichloride rac/meso-ethanediylbis(2-alkyl-4,5,6,7-tetrahydro-1-indenyl)zirconium dichloride rac/meso-dimethylsilanediylbis(2-alkyl-4,5,6,7-tetrahydro-1-indenyl)dimethylzirconium rac/meso-dimethylmethylenebis(2-alkyl-4,5,6,7-tetrahydro-1-indenyl)dimethylzirconium rac/meso-ethanediylbis(2-alkyl-4,5,6,7-tetrahydro-1-indenyl)dimethylzirconium rac/meso-dimethylsilanediylbis(2-alkyl-4,5,6,7-tetrahydro-1-indenyl)hafnium dichloride rac/meso-dimethylmethylenebis(2-alkyl-4,5,6,7-tetrahydro-1-indenyl)hafnium dichloride rac/meso-ethanediylbis(2-alkyl-4,5,6,7-tetrahydro-1-indenyl)hafnium dichloride rac/meso-dimethylsilanediylbis(2-alkyl-4,5,6,7-tetrahydro-1-indenyl)dimethylhafnium rac/meso-dimethylmethylenebis(2-alkyl-4,5,6,7-tetrahydro-1-indenyl)dimethylhafnium rac/meso-ethanediylbis(2-alkyl-4,5,6,7-tetrahydro-1-indenyl)dimethylhafnium In the abovementioned rac/meso-metallocenes, the rac/meso ratio is preferably from >30:1 to <100:1, particularly preferably from >35:1 to <60:1, very particularly preferably from >40:1 to <50:1, and alkyl is linear or branched $C_1$–$C_{10}$-alkyl such as methyl, ethyl, propyl, isopropyl, n-butyl, isobutyl, tert-butyl, pentyl, isopentyl, hexyl or decyl.

Surprisingly, the rac/meso-metallocenes of the present invention can be used directly as catalyst component for preparing highly isotactic polyolefins without it being necessary to isolate the rac form. Such a catalyst system comprises at least one cocatalyst and at least one rac/meso-metallocene. It is also possible to use metallocene mixtures, e.g. mixtures of two or more rac/meso-metallocenes of the formula I or mixtures of one or more rac/meso-metallocenes of the formula I with one or more other metallocenes such as a bisindenyl-metallocene which is substituted in the six-membered ring of the indenyl ligands. Such six-ring-substituted metallocenes are described, for example, in EP-A-0 646 604. Furthermore, the rac/meso-metallocene can also be used in supported form for olefin polymerization.

The cocatalyst component which may be present in the catalyst system comprises at least one compound of the aluminoxane type or another Lewis acid or an ionic non-coordinating compound which reacts with a metallocene to convert it into a cationic compound. As aluminoxane, preference is given to using a compound of the formula II $$(R\text{—}AlO)p \tag{II}$$

Aluminoxanes can be cyclic as in formula III (III)

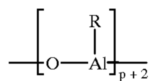

or linear as in formula IV (IV)

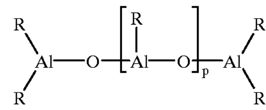

or of the cluster type as in formula V, as is described in relatively recent literature, cf. JACS 117 (1995), 6465–74, Organometallics 13 (1994), 2957-1969.

(V)

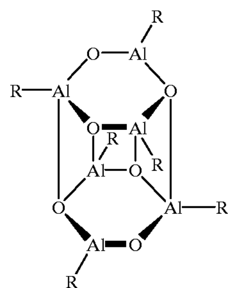

The radicals R in the formulae (II), (III), (IV) and (V) may be identical or different and are each a $C_1$–$C_{20}$-hydrocarbon group such as a $C_1$–$C_{10}$-alkyl group or a $C_6$–$C_{20}$-aryl group, or hydrogen and p is an integer from 2 to 50, preferably from 10 to 35.

Preferably, the radicals R are identical and are methyl, isobutyl, n-butyl, phenyl or benzyl, particularly preferably methyl.

If the radicals R are different, they are preferably methyl and hydrogen, methyl and isobutyl or methyl and n-butyl preferably being present in a proportion of from 0.01 to 40% (number of radicals R).

The aluminoxane can be prepared in various ways. In one known method, an aluminum-hydrocarbon compound and/ or a hydridoaluminum-hydrocarbon compound is reacted with water (gaseous, solid, liquid or bound—for example as water of crystallization) in an inert solvent such as toluene. To prepare an aluminoxane having different alkyl groups R, two different trialkylaluminums ($AlR_3$+$AlR'_3$) corresponding to the desired composition and reactivity are reacted with water (cf. S. Pasynkiewicz, Polyhedron 9 (1990) 429 and EP-A-302 424).

Regardless of the method of preparation, all aluminoxane solutions have in common a varying content of unreacted aluminum starting compound which is present in free form or as adduct.

For the purposes of the present invention, Lewis acids are, apart from aluminoxane, for example other organoaluminum compounds or organoboron compounds which contain $C_1$–$C_{20}$-groups such as branched or unbranched alkyl or haloalkyl, e.g. methyl, propyl, isopropyl, isobutyl or trifluoromethyl, unsaturated groups such as aryl or haloaryl, e.g. phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Particular preference is given to organoboron compounds. Examples of such organoboron compounds are trifluoroborane, triphenylborane, tris(4-fluorophenyl)borane, tris(3,5-difluorophenyl)borane, tris(4-fluorophenyl)borane, tris(pentafluorophenyl)borane, tris(tolyl)borane, tris(3,5-dimethylphenyl)borane, tris(3,5-difluorophenyl)borane and/or tris(3,4,5-trifluorophenyl)borane. Particular preference is given to tris(pentafluorophenyl)borane.

For the purposes of the present invention, ionic non-coordinating cocatalysts are, for example, compounds which contain a non-coordinating anion such as tetrakis(pentafluorophenyl)borate, tetraphenylborate, $SbF_6$—, $CF_3SO_3$— or $ClO_4^-$. As cationic counterion, Lewis acids such as methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or triphenylcarbenium.

Examples of such ionic compounds are triethylammonium tetra(phenyl)borate,
tributylammonium tetra(phenyl)borate,
trimethylammonium tetra(phenyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or N,N-dimethylanilinium tetrakis(pentafluorophenyl)borate. It is also possible to use mixtures of at least one Lewis acid and at least one ionic compound.

As cocatalyst components, borane or carborane compounds such as 7,8-dicarbaundecarborane(13), undecahydrido-7,8-dimethyldicarbaundecaborane, dodecahydrido-1-phenyl-1,3-dicarbanonaborane, tri(butyl)ammonium decahydrido-8-ethyl-7,9-dicarbaundecaborate, 4-carbanonaborane(14), bis(tri(butyl)ammonium)nonaborate, bis(tri(butyl)ammonium) undecaborate, bis(tri(butyl)ammonium)dodecaborate, bis(tri(butyl)ammonium)decachlorodecaborate, tri(butyl)ammonium 1-carbadecaborate, tri(butyl)ammonium 1-carbadodecaborate, tri(butyl)ammonium 1-trimethylsilyl-1-carbadecaborate, tri(butyl)ammonium bis(nonahydrido-1,3-dicarbanonaborato)cobaltate(III), tri(butyl)ammonium bis(undecahydrido-7,8-dicarbaundecaborato)ferrate(III) are likewise of importance.

The rac/meso-metallocene/cocatalyst system can be used in olefin polymerization in unsupported or preferably supported form.

The support component of the catalyst system of the present invention can be any organic or inorganic, inert solid, in particular a porous support such as talc, inorganic oxides or finely divided polymer powder, e.g. polyolefins.

Inorganic oxides of the elements of groups 2, 3, 4, 5, 13, 14, 15 and 16 of the Periodic Table of the Elements are useful as supports. Examples of oxides which are preferred as supports include silicon dioxide, aluminum oxide and also mixed oxides of the two elements and corresponding oxide mixtures. Other inorganic oxides which may be used alone or in combination with the abovementioned preferred oxidic supports are MgO, $ZrO_2$ or $B_2O_3$, to name only a few.

The support materials used have a specific surface area in the range from 10 $m^2/g$ to 1000 $m^2/g$, a pore volume in the range from 0.1 ml/g to 5 ml/g and a mean particle size of from 1 $\mu m$ to 500 $\mu m$. Preference is given to supports having a specific surface area in the range from 50 $m^2/g$ to 500 $m^2/g$, a pore volume in the range from 0.5 ml/g to 3.5 ml/g and a mean particle size in the range from 5 $\mu m$ to 350 $\mu m$. Particular preference is given to supports having a specific surface area in the range from 200 $m^2/g$ to 400 $m^2/g$, a pore volume in the range from 0.8 ml/g to 3.0 ml/g and a mean particle size of from 10 $\mu m$ to 200 $\mu m$.

If the support material used naturally has a low moisture content or residual solvent content, dehydration or drying prior to use can be omitted. If this is not the case, for example when silica gel is used as support material, dehydration or drying is advisable. The weight loss on ignition (LOI) should be 1% or less. Thermal dehydration or drying of the support material can be carried out under reduced pressure and with simultaneous inert gas blanketing, e.g. nitrogen. The drying temperature is in the range from 100° C. to 1000° C., preferably from 200° C. to 800° C. In this case, pressure is not a critical parameter. The duration of the drying process can be from 1 to 24 hours. Shorter or longer drying times are possible provided that the hydroxyl groups on the support surface can reach equilibrium under the conditions selected, which normally requires from 4 to 8 hours.

Dehydration or drying of the support material is also possible by chemical means, by reacting the adsorbed water and the hydroxyl groups on the surface with suitable passivating agents. Reaction with the passivating reagent enables the hydroxyl groups to be converted completely or partly into a form which leads to no negative interaction with the catalytically active centers. Suitable passivating agents are, for example, silicon halides and silanes such as silicon tetrachloride, chlorotrimethylsilane or dimethylaminotrichlorosilane, or organometallic compounds of aluminum, boron and magnesium, e.g. trimethylaluminum, triethylaluminum, triisobutylaluminum, triethylborane, dibutylmagnesium or aluminoxanes such as methylaluminoxane. The chemical dehydration or passivation of the support material can be carried out by reacting a suspension of the support material in a suitable solvent with the passivating reagent in pure form or in solution in a suitable solvent with exclusion of air and moisture. Suitable solvents are aliphatic or aromatic hydrocarbons such as pentane, hexane, heptane, toluene or xylene. The passivation is carried out at from 25° C. to 120° C., preferably from 50° C. to 70° C. Higher and lower temperatures are possible. The reaction time is from 30 minutes to 20 hours, preferably from 1 to 5 hours. After chemical dehydration is complete, the support material is isolated by filtration under inert conditions, washed one or more times with suitable inert solvents as have been described above and subsequently dried in a stream of inert gas or under reduced pressure.

Organic support materials such as finely divided polyolefin powders, for example polyethylene, polypropylene or polystyrene, can also be used and should likewise be freed of adhering moisture, solvent residues or other impurities by appropriate purification and drying operations prior to use.

To prepare the supported catalyst system, it is possible, for example, to bring at least one of the above-described rac/meso-metallocene components in a suitable solvent into contact with the cocatalyst component to give a soluble reaction product. The soluble reaction product is then added to the dehydrated or passivated support material, the solvent is removed and the resulting supported rac/meso-metallocene catalyst system is dried to ensure that the solvent is completely or mostly removed from the pores of the support material. The supported catalyst is obtained as a free-flowing powder.

As an alternative to the above-described process for application to a support, other orders of addition of rac/meso-metallocenes, cocatalysts and supports are also possible.

A preferred method of preparing a free-flowing and, if desired, prepolymerized supported catalyst system comprises the following steps:

a) Preparation of a rac/meso-metallocene/cocatalyst mixture in a suitable solvent (preactivation), where the rac/meso-metallocene component has one of the above-described structures, b) application of the preactivated rac/meso-metallocene/cocatalyst solution to a porous, generally inorganic, dehydrated support, c) removal of the main part of solvent from the resulting mixture, d) isolation of the supported catalyst system, and e) if desired, prepolymerization of the supported catalyst system obtained with one or more olefinic monomer(s) to give a prepolymerized supported catalyst system.

Preferred solvents for the preparation of the preactivated rac/meso-metallocene/cocatalyst mixture are hydrocarbons and hydrocarbon mixtures which are liquid at the reaction temperature selected and in which the individual components preferably dissolve. However, the solubility of the individual components is not a prerequisite as long as it is ensured that the reaction product of rac/meso-metallocene component and cocatalyst component is soluble in the solvent chosen. Examples of suitable solvents include alkanes such as pentane, isopentane, hexane, heptane, octane and nonane, cycloalkanes such as cyclopentane and cyclohexane, and aromatics such as benzene, toluene, ethylbenzene and diethylbenzene. Very particular preference is given to toluene.

The amounts of rac/meso-metallocene and cocatalyst such as aluminoxane used in the preparation of the supported catalyst system can be varied over a wide range. In the case of aluminoxane, preference is given to a molar ratio of aluminum to transition metal in the rac/meso-metallocene of from 10:1 to 1000:1, very particularly preferably from 50:1 to 500:1. In the case of methylaluminoxane, 30% strength toluene solutions are preferably used, but the use of 10% strength solutions is also possible.

The rac/meso-metallocene of the present invention can be preactivated. To preactivate it, the rac/meso-metallocene in the form of a solid can be dissolved in a solution of the cocatalyst such as aluminoxane in a suitable solvent. It is also possible to dissolve the rac/meso-metallocene separately in a suitable solvent and subsequently to combine this solution with the cocatalyst solution, e.g. an aluminoxane solution. It is likewise possible to combine the rac/meso-metallocene-containing reaction mixture obtained in the metallocene synthesis with the cocatalyst solution, e.g. an aluminoxane solution. Preference is given to using toluene. The preactivation time can be from about 1 minute to 200 hours. The preactivation can take place at room temperature (25° C.). The use of higher temperatures can shorten the time required for preactivation in specific cases and effect an additional increase in activity. In this case, higher temperatures means temperatures in a range from 50° C. to 100° C.

The preactivated solution can subsequently be combined with an inert support material, usually silica gel, in the form of a dry powder or as a suspension in one of the abovementioned solvents. Preference is given to using the silica gel in the form of a powder. The order of addition is immaterial. The preactivated metallocene/cocatalyst solution can be added to the support material or else the support material can be introduced into the solution.

The volume of the preactivated solution can exceed 100% of the total pore volume of the support material used or else can be up to 100% of the total pore volume. Preference is given to a range from 100 to 500%, particularly preferably from 110 to 300%, of the total pore volume or else from 50% to 100%, preferably from 70 to 95%.

The temperature at which the preactivated solution is brought into contact with the support material can vary within a range from 0° C. to 100° C. However, lower or higher temperatures are also possible. After the support material and the solution have been combined, the mixture is held at this temperature for a further period of from about 1 minute to 1 hour, preferably 5 minutes.

Subsequently, the solvent is completely or mostly removed from the supported catalyst system; during this procedure, the mixture can be stirred and, if desired, also heated. Preferably, both the visible proportion of solvent and also the proportion present in the pores of the support material are removed. Removal of the solvent can be carried out in a conventional way using reduced pressure and/or purging with inert gas. In the drying procedure, the mixture can be heated until the free solvent has been removed, which usually takes from 1 to 3 hours at a preferred temperature in the range 30° C. to 60° C. The free solvent is the visible proportion of solvent in the mixture. For the purposes of the present invention, residual solvent is the proportion which is enclosed in the pores.

As an alternative to complete removal of the solvent, it is also possible for the supported catalyst system to be dried only to a specific residual solvent content, with the free solvent having been completely removed. The supported catalyst system can subsequently be washed with a low-boiling hydrocarbon such as pentane or hexane and dried again.

The supported catalyst system can either be used directly for polymerization of olefins or be prepolymerized with one or more olefinic monomers before being used in a polymerization process. For the prepolymerization, the supported catalyst system is, for example, suspended in an inert hydrocarbon such as hexane and prepolymerized at from 0° C. to 60° C. in the presence of at least one olefin such as ethylene, propylene, hexene, butene or 4-methyl-1-pentene. The prepolymerized catalyst system can subsequently be dried until it is free flowing. Alternatively, this suspension can be used directly for polymerization. A further possible variant of the prepolymerization is to prepolymerize the catalyst system in the gas phase. For this purpose, at least one olefin as defined above is passed through the pulverulent catalyst system while stirring.

As additive, a small amount of an α-olefin such as styrene as activity-increasing component or an antistatic can be added during or after the preparation of the supported catalyst system.

The present invention also provides a process for preparing a polyolefin by polymerization of one or more olefins in the presence of the catalyst system of the present invention comprising at least one rac/meso-metallocene of the formula I. For the purposes of the present invention, the term polymerization includes both homopolymerization and copolymerization.

The supported catalyst system can be used for the polymerization of olefins in combination with an aluminum alkyl or an aluminoxane as scavenger. The soluble aluminum components are added to the monomers and serve to free the monomers of substances which can impair the catalyst activity. The amount of aluminum component added depends on the quality of the monomers used.

Preference is given to polymerizing olefins of the formula $R^a$—CH═CH—$R^b$, where $R^a$ and $R^b$ are identical or different and are each a hydrogen atom or a carbon-containing radical having from 1 to 20 carbon atoms, in particular from 1 to 10 carbon atoms, and $R^a$ and $R^b$ together with the atoms connecting them can form one or more rings.

Examples of such olefins are 1-olefins having from 2 to 40, preferably from 2 to 10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene or ethylnorbornadiene and cyclic olefins such as norbornene, tetracyclododecene or methylnorbornene. In the process of the present invention, preference is given to homopolymerizing propene or ethene or copolymerizing propene with ethene and/or with one or more 1-olefins having from 4 to 20 carbon atoms, e.g. hexene, and/or one or more dienes having from 4 to 20 carbon atoms, e.g. 1,4-butadiene, norbornadiene, ethylidenenorbornene or ethylnorbornadiene. Examples of such copolymers are ethylene-propene copolymers or ethene-propene-1,4-hexadiene terpolymers.

The polymerization is carried out at from −60° C. to 300° C., preferably from 50° C. to 200° C., very particularly preferably from 50° C. to 80° C. The pressure is from 0.5 bar to 2000 bar, preferably from 5 bar to 64 bar.

The polymerization can be carried out in solution, in bulk, in suspension or in the gas phase, continuously or batchwise and in one or more stages.

If necessary, hydrogen is added as molar mass regulator and/or to increase the activity.

The polymers prepared using the catalyst system of the present invention display a uniform particle morphology and contain no fines. No deposits or caked material are formed in the polymerization using the catalyst system of the present invention.

The catalyst system of the present invention enables highly isotactic polyolefins such as polypropylene to be obtained with high stereospecificity and regiospecificity.

The invention is illustrated by the following examples.

All glassware was baked out under reduced pressure and flushed with argon. All operations were carried out with exclusion of moisture and oxygen in Schlenk vessels. The solvents used were freshly distilled over Na/K alloy under argon and stored under argon in Schlenk vessels.

Abbreviations

VN=viscosity number in $cm^3/g$ $M_w$=weight average molar mass in g/mol (determined by gel permeation chromatography)

$M_w/M_n$=polydispersity m.p.=melting point in °C. (determined by DSC, 20° C./min heating/cooling rate II=isotactic index (II=mm+0.5 mr)

$n_{iso}$=isotactic block length ($n_{iso}$=1+[2 mm/mr])

II and $n_{iso}$ determined by $^{13}$C-NMR spectroscopy Determination of the rac:meso ratios by means of $^1$H-NMR.

Synthesis of Rac/meso-metallocenes

EXAMPLE A rac/meso-Dimethylsilanediylbis(4,5,6,7-tetrahydro-1-indenyl)zirconium dichloride (1)

A solution of 50 g (387 mmol) of indene (90% pure) in 320 ml of toluene and 48 ml of THF was mixed at room temperature with 150 ml (400 mmol) of a 20% strength solution of butyllithium in toluene and the mixture was stirred for a further period of one hour at room temperature. Subsequently, the suspension was cooled to −10° C. and treated with 23.5 ml (200 mmol) of dimethyldichlorosilane. After stirring for another hour, 150 ml (400 mmol) of a 20% strength solution of butyllithium in toluene were added and the reaction mixture was stirred for a further 1 hour. 46 g (197 mmol) of zirconium tetrachloride were added to the reaction mixture and the orange suspension was stirred for a further period of 2 hours at room temperature, filtered and washed with 100 ml of THF. The filter cake, viz. rac/meso-dimethylsilanediylbisindenylzirconium dichloride was suspended in 500 ml of toluene together with 1.5 g (1.4 mmol) of palladium (10% on activated carbon) and hydrogenated at 70° C. and a hydrogen pressure of 20 bar. After 5 hours, the reaction mixture was filtered hot, evaporated to half its volume and crystallized at 0–5° C. This gave 35.3 g (39% based on indene) of rac/meso-dimethylsilanediylbis(4,5,6,7-tetrahydro-1-indenyl)zirconium dichloride (1) (rac/meso=38:1).

Polymerization Examples

EXAMPLE 1

A dry 24 $dm^3$ reactor was flushed with propylene and charged with 12 $dm^3$ of liquid propylene and 25 $cm^3$ of methylaluminoxane solution in toluene (corresponding to 37 mmol of Al, mean degree of oligomerization p=22). The contents of the reactor were stirred at 30° C. for 5 minutes at 250 rpm. In parallel thereto, 5 mg of the metallocene dimethylsilanediylbis(4,5,6,7-tetrahydro-1-indenyl) zirconium dichloride (from Example A, compound (1), rac/meso=38:1 mixture) were dissolved in 10 $cm^3$ of methylaluminoxane solution in toluene (17 mmol of Al) and preactivated by being allowed to stand for 5 minutes. The solution was introduced into the reactor and polymerization was carried out for one hour at 70° C. This gave 2.03 kg of polymer. The metallocene activity was 406 kg of PP/g of met. The following properties were determined on the polymer:

VN=42 $cm^3$/g; molar mass Mw=32500 g/mol, Mw/Mn=1.9; melting point=140° C.; II=94.8%; $n_{iso}$=35.

EXAMPLE 2

Preparation of the Supported Catalyst System 86 mg (0.18 mmol) of dimethylsilanediylbis(2-ethyl-1-indenyl)zirconium dichloride and 82 mg (0.18 mmol) of dimethylsilanediylbis(4,5,6,7-tetrahydro-1-indenyl) zirconium dichloride (from Example A, rac/meso=38:1) were dissolved at room temperature in 18 $cm^3$ (84 mmol of Al) of a 30% strength solution of methylaluminoxane in toluene[1]). The mixture was diluted with 50 $cm^3$ of toluene and stirred at 25° C. for 10 minutes. 15 g of $SiO_2$[2]) were slowly introduced into this solution. After the addition was complete, the mixture was stirred for 5 minutes at room temperature. The mixture was subsequently evaporated to dryness at 40° C. under reduced pressure (2 hours) and the residue was dried for 5 hours at 25° C. and $10^{-3}$ mbar. This gave 23 g of a free-flowing, orange-pink powder which, according to elemental analysis, contained 0.16% by weight of Zr and 9.6% by weight of Al.

Polymerization

A dry 16 $dm^3$ reactor which had first been flushed with nitrogen and subsequently with propene was charged with 10 $dm^3$ of liquid propene. 8 $cm^3$ of 20% strength triethylaluminum solution in Varsol (Witco) were added as scavenger and the mixture was stirred for 15 minutes at 30° C. Subsequently, a suspension of 1.5 g of the supported metallocene catalyst in 20 $cm^3$ of Exxsol was introduced into the reactor and the polymerization system was heated to the polymerization temperature of 65° C. and held at 65° C. for 1 hour. The polymerization was stopped by venting the excess monomer and the polymer obtained was dried under reduced pressure. This gave 3.1 kg of polypropylene powder. The catalyst activity was 288 kg of PP/(g of met.×h) or 2.1 kg of PP/(g of cat.×h). The isotactic polypropylene prepared had the following properties: m.p.=146° C.; $M_w$=180,000 g/mol, $M_w/M_n$=3.6; VN=140 $cm^3$/g, bulk density=370 g/$dm^3$.

[1], Albemarle Corporation, Baton Rouge, La., USA

[2], Silica type MS 948 , W. R. Grace, Davison Chemical Division, Baltimore, Md., USA, pore volume=1.6 ml/g, calcined at 800° C.

EXAMPLE 3

Preparation of the Supported Catalyst System

Example 2 was repeated using 113 mg (0.18 mmol) of dimethylsilanediylbis(2-methyl-4-phenyl-1-indenyl) zirconium dichloride and 82 mg (0.18 mmol) of dimethylsilanediylbis(4,5,6,7-tetrahydro-1-indenyl) zirconium dichloride (from Example A, rac/meso=38:1). This gave 24 g of a free-flowing, red-orange powder which, according to elemental analysis, contained 0.15% by weight of Zr and 10.1% by weight of Al.

Polymerization

The polymerization was carried out using a method analogous to Example 2. This gave 3.2 kg of polypropylene powder. The catalyst activity was 258 kg of PP/(g of met.×h) or 2.1 kg of PP/(g of cat.×h). The isotactic polypropylene prepared had the following properties: m.p.=147° C.; $M_w$=480,000 g/mol, $M_w/M_n$=4.7, VN=430 $cm^3$/g, bulk density=360 g/$dm^3$.

We claim:

1. A process for preparing a rac/meso-metallocene of formula I

Formula I

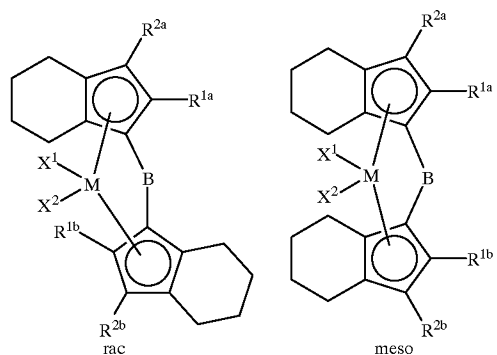

having a rac/meso ratio of from 20:1 to 200:1, wherein

M is a metal of groups IIIb, IVb, Vb or VIb of the Periodic Table of the Elements, $X^1$ and $X^2$ are identical or different and are each a hydrogen atom, a group comprising from 1 to 40 carbon atoms, an OH group, a halogen atom or a pseudohalogen, $R^{1a}$, $R^{1b}$, $R^{2a}$, and $R^{2b}$ are identical or different and are each a hydrogen atom, a group comprising from 1 to 40 carbon atoms, an OH group, a halogen atom or a pseudohalogen, or a $NR^5_2$, $SR^5$, $OSiR^5_3$, $SiR^5_3$ or $RR^5_2$ group, and $R^5$ is one of the radicals set forth for $X^1$, B is a single- to four membered bridging moiety, comprising the steps:

a) reacting a cyclopentadiene of formula A (A)

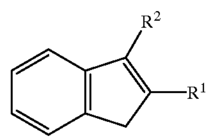

wherein $R^1$ is one of the radicals $R^{1a}$ or $R^{1b}$, and $R^2$ is one of the radicals $R^{2a}$ or $R^{2b}$, with a bridging reagent $BY_2$ wherein Y is a leaving group, to form a bridged biscyclopentadienyl ligand system, b) reacting the bridged biscyclopentadienyl ligand system with a metal halide to form a metallocene of formula Ia Formula Ia

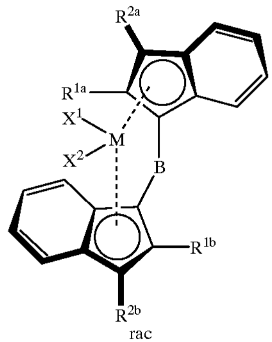

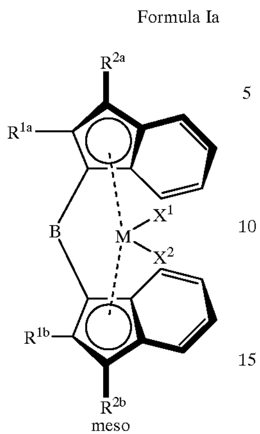

wherein $X^1$ and $X^2$ are halogen, c) hydrogenating the metallocene of formula Ia to form a metallocene of formula Ib Formula Ib

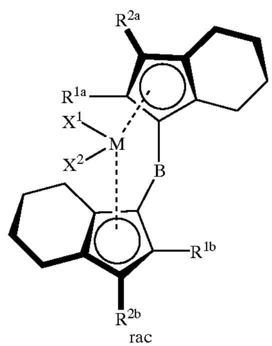

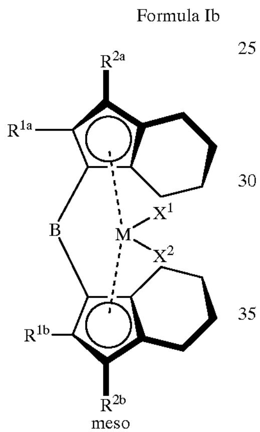

d) and, optionally, reacting the metallocene of formula Ib with an organometallic compound $R^3M^1$ wherein $R^3$ is a radical $X^1$ or $X^2$ different from halogen, and $M^1$ is an element of main group I, II or III of the Periodic Table of the Elements, to form a metallocene Ic Formula Ic

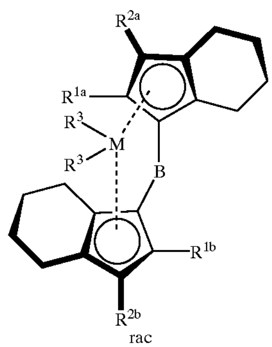

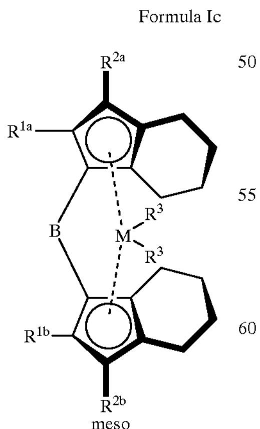

wherein all steps are carried out in the same solvent or solvent mixture.

2. The process of claim 1, wherein $X^1$ and $X^2$ are identical or different and are each a hydrogen atom, $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen, $R^{1a}$, $R^{1b}$, $R^{2a}$ and $R^{2b}$ are identical or different and are each a hydrogen atom, $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen, or a $NR^5_2$, $SR^5$, $OSiR^5_3$, $SiR^5_3$ or $RR^5_2$ group, and $R^5$ is one of the radicals set forth for $X^1$,

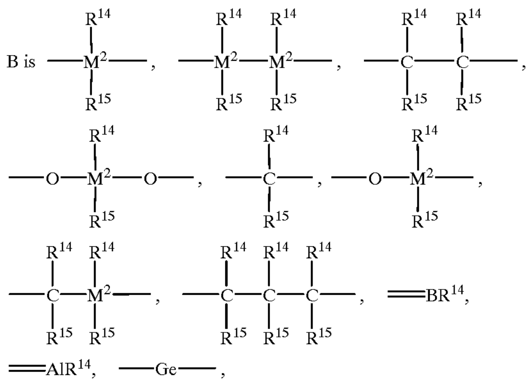

—O—, —S—, =SO, $=SO_2$, $=NR^{14}$, =CO, $=PR^{14}$ or $=P(O)R^{14}$, wherein $R^{14}$ and $R^{15}$ are identical or different and are each a hydrogen atom, a halogen atom or a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_6$–$C_{10}$-aryl group, A $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group, a $C_7$–$C_{40}$-alkylaryl group, or $R^{14}$ and $R^{15}$ together with the atoms connecting them form a ring, and $M^2$ is silicon, germanium or tin.

3. The process of claim 1, wherein the leaving group Y is halogen.

4. A chiral rac/meso-metallocene of formula I having a rac/meso ratio of from 20:1 to 200:1

Formula I

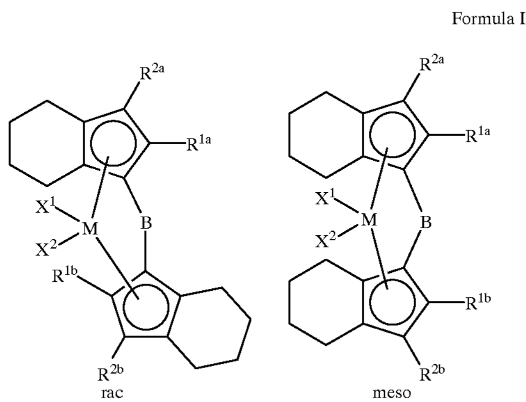

wherein

M is a metal of groups IIIb, IVb, Vb or VIb of the Periodic Table of the Elements, $X^1$ and $X^2$ are identical or different and are each a hydrogen atom, a group comprising from 1 to 40 carbon atoms, an OH group, a halogen atom or a pseudohalogen, $R^{1a}$, $R^{1b}$, $R^{2a}$ and $R^{2b}$ are identical or different and are each a hydrogen atom, a group comprising from 1 to 40 carbon atoms, an OH group, a halogen atom or a pseudohalogen, or a $NR^5_2$, $SR^5$, $OSiR^5_3$, $SiR^5_3$ or $RR^5_2$ group, and $R^5$ is one of the radicals set forth for $X^1$, B is a single- to four membered bridging moiety.

5. The rac/meso-metallocene of formula I defined in claim 4, wherein $X^1$ and $X^2$ are identical or different and are each a hydrogen atom, $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen, $R^{1a}$, $R^{1b}$, $R^{2a}$ and $R^{2b}$ are identical or different and are each a hydrogen atom, $C_1$–$C_{10}$-alkyl, $C_1$–$C_{10}$-alkoxy, $C_6$–$C_{20}$-aryl, $C_6$–$C_{20}$-aryloxy, $C_2$–$C_{10}$-alkenyl, $C_7$–$C_{40}$-arylalkenyl, $C_7$–$C_{40}$-alkylaryl or $C_8$–$C_{40}$-arylalkenyl, an OH group, a halogen atom or a pseudohalogen, or a $NR^5_2$, $SR^5$, $OSiR^5_3$, $SiR^5_3$ or $RR^5_2$ group, and $R^5$ is one of the radicals set forth for $X^1$,

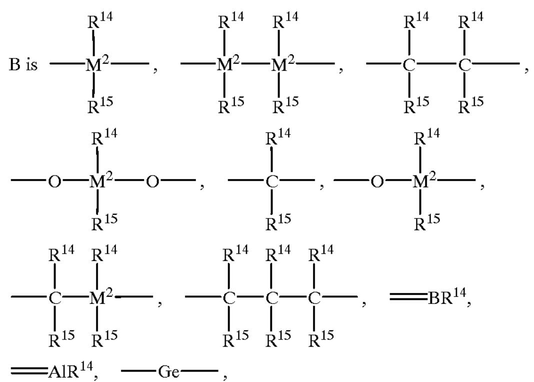

—O—, —S—, =SO, $=SO_2$, $=NR^{14}$, =CO, $=PR^{14}$ or $=P(O)R^{14}$, wherein $R^{14}$ and $R^{15}$ are identical or different and are each a hydrogen atom, a halogen atom or a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_6$–$C_{10}$-aryl group, A $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group, a $C_7$–$C_{40}$-alkylaryl group, or $R^{14}$ and $R^{15}$ together with the atoms connecting them form a ring, and $M^2$ is silicon, germanium or tin.

6. The rac/meso-metallocene of formula I defined in claim 4, wherein

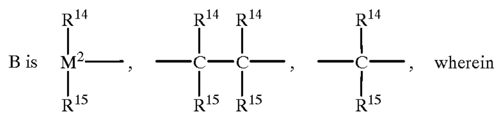

$M^2$ is silicon or germanium, and $R^{14}$ and $R^{15}$ are identical or different and are hydrogen, a $C_1$–$C_4$-alkyl group, a $CF_3$ group, a $C_6$–$C_8$-aryl group, a pentafluorophenyl group, a $C_1$–$C_{10}$-, alkoxy group, a $C_2$–$C_4$-alkenyl group, a $C_7$–$C_{10}$-arylalkyl group, a $C_8$–$C_{12}$-arylalkenyl group or a $C_7$–$C_{12}$-alkylaryl group.

7. The rac/meso-metallocene of formula I defined in claim 4, wherein

B is $R^{14}R^{15}C=$, $R^{14}R^{15}Si=$ or $—CR^{14}R^{15}—CR^{14}R^{15}—$ bridge, where $R^{14}$ and $R^{15}$ are identical or different and are each a hydrogen atom, a $C_1$–$C_4$-alkyl group or a $C_6$–$C_{10}$-aryl group.

8. The rac/meso-metallocene of formula I defined in claim 4, wherein B is $—CH_2—CH_2—$, $(H_3C)_2Si=$ or $(H_3C)_2C=$.

9. The rac/meso-metallocene of formula I defined in claim 4, wherein $MX^1X^2$ represents $ZrCl_2$, $HfCl_2$, $Zr(CH_3)_2$ or $Hf(CH_3)_2$.

10. A catalyst comprising a) at least one chiral rac/meso-metallocene of formula I as defined in claim 4 and b) at least one cocatalyst.

11. The catalyst defined in claim 10 which further comprises a support.

12. The catalyst defined in claim 10, in prepolymerized form.

13. A process for the polymerization of olefins, wherein the olefins are polymerized in the presence of the catalyst defined in claim 10.

* * * * *